United States Patent
Calvert et al.

(10) Patent No.: US 10,123,957 B2
(45) Date of Patent: Nov. 13, 2018

(54) TRANSPARENT COSMETIC AND PERSONAL CARE COMPOSITIONS

(71) Applicant: Conopco, Inc., Englewood Cliffs, NJ (US)

(72) Inventors: Ralph Calvert, Wirral (GB); Joanne Louise Cook, Wirral (GB); Richard Mackenzie Read, Tarporley (GB); Hannah Mary Southey, Great Sutton (GB); Stephen Lee Wire, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/505,195

(22) PCT Filed: Aug. 28, 2015

(86) PCT No.: PCT/EP2015/069799
§ 371 (c)(1),
(2) Date: Feb. 20, 2017

(87) PCT Pub. No.: WO2016/034519
PCT Pub. Date: Mar. 10, 2016

(65) Prior Publication Data
US 2017/0246097 A1 Aug. 31, 2017

(30) Foreign Application Priority Data
Sep. 3, 2014 (EP) .................................. 14183458

(51) Int. Cl.

| | |
|---|---|
| *A61K 8/60* | (2006.01) |
| *A61K 8/92* | (2006.01) |
| *A61K 8/23* | (2006.01) |
| *A61K 8/49* | (2006.01) |
| *A61K 8/39* | (2006.01) |
| *A61Q 5/12* | (2006.01) |
| *A61Q 5/00* | (2006.01) |
| *A61Q 5/02* | (2006.01) |
| *A61Q 5/06* | (2006.01) |
| *A61K 8/64* | (2006.01) |
| *A61Q 19/00* | (2006.01) |
| *A61K 8/81* | (2006.01) |
| *A61K 8/86* | (2006.01) |
| *A61Q 19/10* | (2006.01) |
| *A61K 8/04* | (2006.01) |
| *A61K 8/19* | (2006.01) |

(52) U.S. Cl.
CPC ............... *A61K 8/60* (2013.01); *A61K 8/042* (2013.01); *A61K 8/19* (2013.01); *A61K 8/23* (2013.01); *A61K 8/39* (2013.01); *A61K 8/498* (2013.01); *A61K 8/64* (2013.01); *A61K 8/8164* (2013.01); *A61K 8/86* (2013.01); *A61K 8/922* (2013.01); *A61Q 5/002* (2013.01); *A61Q 5/006* (2013.01); *A61Q 5/02* (2013.01); *A61Q 5/06* (2013.01); *A61Q 5/12* (2013.01); *A61Q 19/00* (2013.01); *A61Q 19/10* (2013.01); *A61K 2800/262* (2013.01); *A61K 2800/43* (2013.01); *A61K 2800/48* (2013.01); *A61K 2800/49* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,145,607 A * | 9/1992 | Rich ..................... | A61K 8/416 424/70.12 |
| 5,158,699 A | 10/1992 | MacGilp et al. | |
| 5,607,980 A | 3/1997 | McAtee et al. | |
| 5,968,528 A | 10/1999 | Deckner et al. | |
| 6,048,520 A * | 4/2000 | Hoshowski ............. | A61K 8/11 424/70.1 |
| 2002/0012645 A1 | 1/2002 | Midha et al. | |
| 2002/0035046 A1* | 3/2002 | Lukenbach ............. | A61K 8/49 510/122 |
| 2002/0061500 A1 | 5/2002 | Collopy | |
| 2003/0171230 A1 | 9/2003 | Shana'a et al. | |
| 2004/0081633 A1 | 4/2004 | Mercier et al. | |
| 2005/0008681 A1 | 1/2005 | Deckner et al. | |

(Continued)

FOREIGN PATENT DOCUMENTS

| | | |
|---|---|---|
| EP | 1330228 | 7/2003 |
| EP | 2025331 | 2/2009 |

(Continued)

OTHER PUBLICATIONS

Alkylpolyglycoside, Wikipedia, Jan. 11, 2015, XP002736673, pp. 1-4, http://de.wikipedia.org/wiki/Alkylpolyglycoside.
Arlasolve 200, Handbook of Industrial Surfactants, 2000, XP002736593, PP88, vol. 1, Third Edition.
Silicone Fluid—DM-Fluid, Shin-Etsu Silicone Technical Data, 2005, pp. 1-36; XP002736312; www.shinetsusilicones.com/files/dmCet.pdf.
Written Opinion in EP14183459, dated Mar. 3, 2015.
IPRP in PCTEP2015069801, Mar. 7, 2017.
IPRP2 in PCTEP2015069799, Nov. 18, 2016.
Search Report (Partial) in PCTEP2015069799, dated Dec. 3, 2015.
Search Report and Written Opinion in EP14183458, dated Jul. 13, 2015.

(Continued)

*Primary Examiner* — Aradhana Sasan
(74) *Attorney, Agent, or Firm* — Karen E. Klumas

(57) ABSTRACT

A transparent cosmetic or personal care composition comprising: a) a polymeric thickener, b) a protein, c) an active material, which is selected from disaccharides, lactones, inorganic salts, diacids and mixtures thereof, d) a solubilizer, e) a pH adjuster, f) a dye g) water wherein the solubilizer comprises a mixture of at least two components, said mixture comprising at least one high HLB component having an HLB value of from 10 to 20 and at least one low HLB component having an HLB value of from 1 to less than 10, and wherein the dye comprises violet, blue, red or mixtures thereof.

8 Claims, No Drawings

(56) References Cited

U.S. PATENT DOCUMENTS

| | | | |
|---|---|---|---|
| 2006/0264344 A1* | 11/2006 | Goldberg | G02B 6/3878 510/130 |
| 2007/0190012 A1 | 8/2007 | Feng et al. | |
| 2009/0214628 A1 | 8/2009 | de Rijk | |
| 2012/0208898 A1 | 8/2012 | Dong et al. | |

FOREIGN PATENT DOCUMENTS

| | | |
|---|---|---|
| EP | 1733717 | 6/2012 |
| EP | 1172083 | 4/2014 |
| JP | 2091016 | 3/1990 |
| JP | 8143420 | 6/1996 |
| JP | 2001302463 | 10/2001 |
| KR | 20140092425 | 7/2014 |
| WO | WO9629979 | 10/1996 |
| WO | WO9632924 | 10/1996 |
| WO | WO9808601 | 3/1998 |
| WO | WO0134111 | 5/2001 |
| WO | WO0236086 | 5/2002 |
| WO | WO2012154505 | 11/2012 |

OTHER PUBLICATIONS

Search Report and Written Opinion in PCTEP2015069799, dated Feb. 12, 2016.
Search Report and Written Opinion in PCTEPP2015069801, Oct. 13, 2015.
Search Report in EP14183458, dated Mar. 6, 2015.
Search Report in EP14183459, dated Mar. 3, 2015.
Written Opinion in PCTEP2015069799, dated Aug. 2, 2016.
Co-Pending Application, Ralph Calvert, U.S. Appl. No. 15/505,201, filed Feb. 20, 2017.
Gelest Silicone Fluids. http://www.gelest.com/wp-content/uploads/Goods-PDF-brochures-inert_silicones_2013.pdf, accessed Jul. 7, 2017, published 2012, 32 printed pages.
Brij®93; Handbook of Industrial Surfactants ; 2000; XP002736594, pp. 122; vol. 1 Third Edition.

\* cited by examiner

TRANSPARENT COSMETIC AND PERSONAL CARE COMPOSITIONS

TECHNICAL FIELD

This invention relates to a transparent cosmetic or personal care composition, to a method of treating surfaces with said composition and to the use of additive materials, for example protein, actives and perfume, in transparent cosmetic and personal care compositions to repair damage in hair.

BACKGROUND

Cosmetic and personal care compositions are often required to have multiple visual and functional attributes. For example, shampoo and hair conditioner compositions are generally required to have properties in addition to their ability to clean and/or condition hair in order to be appealing to the consumer.

Clear, transparent compositions are often desirable visually, but difficult to formulate when additional benefit agents, such as silicones, are incorporated without causing undesirable effects such as clouding and discoloration.

It is known that gel particles can be incorporated into hair treatment compositions. Our European patent EP1330228, discloses the use of shear gels in hair treatment compositions.

We have found that the incorporation of proteins into transparent gels causes discoloration of the gel over time and that the incorporation of perfume causes turbidity.

There remains a need for improved transparent cosmetic and personal care compositions, which can deliver functional benefit agents.

We have now found that a gel containing actives such as protein and fragrance, with enduring visual integrity, can be provided by the use of a solubiliser which comprises a mixture of at least 2 components, said mixture comprising at least one high HLB component and at least one low HLB component.

DEFINITION OF THE INVENTION

According to the present invention, in a first aspect, there is provided a transparent cosmetic or personal care composition comprising:
a) a polymeric thickener,
b) a protein,
c) an active material, which is selected from disaccharides, lactones, inorganic salts, diacids and mixtures thereof,
d) a solubiliser,
e) a pH adjuster,
f) a dye
g) water
wherein the solubiliser comprises a mixture of at least two components, said mixture comprising at least one high HLB component having an HLB value of from 10 to 20 and at least one low HLB component having an HLB value of from 1 to less than 10,
and
wherein the dye comprises violet, blue, red or mixtures thereof.

In a second aspect, the invention provides a method of treating hair comprising applying to the hair a composition in accordance with the first aspect of the invention.

A further aspect of the invention is the use of protein, disaccharides, lactones, inorganic salts, diacids and mixtures thereof in a transparent cosmetic or personal care composition to repair damage in hair.

The Polymer System

The cosmetic and personal care compositions of the present invention comprise water, typically in an amount of from 0.1 wt % to 99 wt %, preferably from 0.5 wt % to 98 wt %, most preferably from 25 wt % to 85 wt %, by weight of the total composition.

The compositions of the invention also comprise at least one polymeric thickener that is responsible for the gelled structure of the composition. The polymeric thickener may be a natural or synthetic polymer, preferably synthetic. Preferred synthetic polymers include hydrophobically modified ethoxylated urethane (HEUR), carbomers, polyvinylpyrrolidone (PVP), cross linked vinyl pyrrolidone copolymers and copolymers of vinyl methyl ether and maleic anhydride, most preferably copolymers of vinyl methyl ether and maleic anhydride, a suitable example being polyvinylmethylether/maleicanhydride decadiene crosspolymer (PVM/MA decadiene crosspolymer), available for example from Ashland Inc. Natural polymers include, for example, a protein or a polysaccharide, preferably kappa-carrageenan, gellan, gelatin, alginate, and mixtures thereof, more preferably gellan, kappa-carrageenan and mixtures thereof, with kappa-carrageenan being particularly preferred.

The polymeric thickener may form a gel alone or may require the addition of another substance, such as, for example, another polymer or a metal ion, for example an alkali metal or an alkaline earth metal, in order for gelation to take place. Conditions under which polymeric thickener can be caused to form a gel are well known to those skilled in the art.

Gelation to form the gelled compositions of the invention can be carried out in any suitable way. The gelation treatment is preferably selected from the group comprising temperature treatment, chemical gelation or crystallisation, preferably chemical. The gelation method that is selected in any given case depends on the ingredients of the final composition.

Gelation by temperature treatment is preferred if the gelling polymer is dependent on temperature for its gel formation. Examples of such gelling agents include gelatin, which gels at a temperature of below about 40° C., agar which forms a gel at a temperature of below about 45° C. and carrageenan or gellan, for which gelation temperature is dependent on salt type and concentration, as described in Handbook of Hydrocolloids, Ed Phillips and Williams, CRC Press, the contents of which are incorporated by reference herein. Proteins that gel or form a network on heat treatment are also suitable for the formation of the polymer system.

It will be appreciated that the exact gelling temperature for the gelling polymer will be determined by, amongst other properties, quality, purity, concentration, solvent properties (such as added solutes and co-solvents) and pH.

Alternatively, the gelling polymer may form a gel by interaction with another component. Typically, such gelling polymers are those polymers which, after being dispersed in another phase, such as a liquid, will set to a gel when allowed to interact with a supplementary active component. The active component is typically a metal cation.

Alternatively, the active component may cause the polymer to gel as a result of a chemical reaction such as oxidation. A further example of a gelling polymer of this type is the class of polymers that gel upon a change in pH, for example polymers, which set or precipitate at a pH below their isoelectric point.

The use of polymers that require a metal cation for gelation is typically preferred. The gelation can be effected by combining the gelling polymer with a salt having a suitable cation. The cation is preferably selected from calcium and potassium ions. Potassium ions are used to cause, for example, gelation of kappa-carrageenan.

The Solubiliser

The cosmetic and personal care compositions of the invention comprise a solubiliser. The solubiliser enables oils to be incorporated into the composition and also reduces turbidity.

The solubiliser comprises a mixture of at least two components, said mixture comprising at least one high HLB component having an HLB value of from 10 to 20 and at least one low HLB component having an HLB value of from 1 to less than 10.

Preferably the solubiliser comprises from 2 to 10, more preferably from 2 to 4 components, said mixture comprising at least one high HLB component having an HLB value of from 10 to 20 and at least one low HLB component having an HLB value of from 1 to less than 10.

High HLB materials have an HLB of from 10 to 20, preferably from 10 to 18.

Suitable high HLB materials include the following:—
PEG-7 Glyceryl Cocoate HLB=10
PEG-20 Almond Glycerides HLB=10
PEG-7 Glyceryl Cocoate (HLB 10),
Coceth-7 (HLB ca. 10)
PEG-25 Hydrogenated Castor Oil HLB=10.8
Stearamide MEA HLB=11
Glyceryl Stearate (and) PEG-100 Stearate HLB=11
Polysorbate 85 HLB=11
PEG-7 Olivate HLB=11
Cetearyl Glucoside HLB=11
PEG-8 Oleate HLB=11.6
Polyglyceryl-3 Methyglucose Distearate=12
Oleth-10 HLB=12.4
Oleth-10/Polyoxyl 10 Oleyl Ether NF HLB=12.4
Ceteth-10 HLB=12.9
PEG-8 Laurate HLB=13
Cocamide MEA HLB=13.5
PEG 40 Hydrogenated Castor Oil (HLB 14-16),
Polysorbate 60 NF HLB=14.9
Polysorbate 60 HLB=14.9
Polysorbate 80 HLB=15
Isosteareth-20 HLB=15
PEG-60 Almond Glycerides HLB=15
Polysorbate 80 NF HLB=15
PEG-20 Methyl Glucose Sesquistearate HLB=15
Ceteareth-20 HLB=15.2
Oleth-20 HLB=15.3
Steareth-20 HLB=15.3
Steareth-21 HLB=15.5
Ceteth-20 HLB=15.7
Isoceteth-20 HLB=15.7
Polysorbate 20 HLB=16.7
Polysorbate 20 NF HLB=16.7
Laureth-23 HLB=16.9
PEG-100 Stearate HLB=18.8
Steareth-100 HLB=18.8
PEG-80 Sorbitan Laurate HLB=19.1

Preferred high HLB materials include:
polyoxyethylene derivatives of sorbitan monolaurate (polysorbate surfactants), preferably selected from Polysorbate 80 (HLB 15) and Polysorbate 20 (HLB 16.7);
PEG 40 Hydrogenated Castor Oil (HLB 14-16),
PEG-7 Glyceryl Cocoate (HLB 10),
Coceth-7 (HLB ca. 10)

Low HLB materials have an HLB of from 1 to less than 10, preferably from 1 to 9.9, preferably from 2 to 9.

Examples of suitable low HLB materials include the following:—
Glycol Distearate HLB=1
Sorbitan Trioleate HLB=1.8
Propylene Glycol Isostearate HLB=2.5
Glycol Stearate HLB=2.9
Sorbitan Sesquioleate HLB=3.7
Glyceryl Stearate HLB=3.8
Lecithin HLB=4
Sorbitan Oleate HLB=4.3
Sorbitan Monostearate NF HLB=4.7
Sorbitan Stearate HLB=4.7
Sorbitan Isostearate HLB=4.7
Steareth-2 HLB=4.9
Oleth-2 HLB=4.9
Glyceryl Laurate HLB=5.2
Ceteth-2 HLB=5.3
PEG-30 Dipolyhydroxystearate HLB=5.5
Glyceryl Stearate SE HLB=5.8
PPG-1-PEG-9 Lauryl Glycol Ether, (HLB ca. 6)
Sorbitan Stearate (and) Sucrose Cocoate HLB=6
PEG-4 Dilaurate HLB=6
Methyl Glucose Sesquistearate HLB=6.6
Lecithin HLB (variable)
PEG-8 Dioleate HLB=8
Sorbitan Laurate HLB=8.6
PEG-40 Sorbitan Peroleate HLB=9
Laureth-4 HLB=9.7
PPG-Laureth-5

Preferred low HLB materials include:
Sorbitan Oleate, (HLB 4.3), PPG-1-PEG-9 Lauryl Glycol Ether, (HLB ca. 6) and PPG-Laureth-5.

The solubiliser is most preferably a mixture of Coceth-7, PPG-1-PEG-9 Lauryl Glycol Ether and PEG-40 Hydrogenated Castor Oil. A suitable solubiliser is sold commercially as Eumulgin HPS®, available from BASF.

The solubiliser is preferably present in an amount of 0.1 to 10 wt %, more preferably from 1.0 to 5 wt %, most preferably from 1.5 to 2 wt %, by weight of the total composition.

The Protein

The cosmetic and personal care compositions of the invention comprise a protein or mixtures thereof. Preferably, the protein is selected from hydrolysed keratin, hydrolysed wheat protein, hydrolysed roe, caviar, hydrolysed elastin and hydrolysed collagen.

The protein is preferably present in a total amount of 0.1 to 10 wt %, more preferably from 0.1 to 5 wt %, most preferably from 0.2 to 2 wt %, by weight of the total composition.

The Active Material

The cosmetic and personal care compositions of the invention comprise an active material, which is selected from lactones, disaccharides, inorganic salts, diacids and mixtures thereof, preferably selected from lactones, disaccharides, inorganic salts and mixtures thereof.

Lactones

Examples of suitable lactones include:

(a) Aldonic Acid Lactones

Aldonic acids are polyhydroxy acids resulting from oxidation of the aldehyde group of an aldose to a carboxylic acid group, and the acid of which can be represented by the following general formula:

$$R(CHOH)_nCH(OH)COOH$$

where R is H or an alkyl group (usually H) and n is an integer from 1 to 6.

The aldonic acids form intramolecular lactones by removing one mole of water between the carboxyl group and one hydroxyl group.

The following are representative aldonic acid lactones:
2,3-dihydroxypropanoic acid lactones (glyceric acid lactone);
2,3,4-trihydroxybutanoic acid lactones (stereoisomers: erythronolactone, threonolactone);
2,3,4,5-tetrahydroxypentanoic acid lactones (stereoisomers: ribonolactone, arabinolactone, xylonolactone, lyxonolactone);
2,3,4,5,6-pentahydroxyhexanoic acid lactones (stereoisomers: allonolactone, altronolactone, gluconolactone, mannonolactone, gulonolactone, idonolactone, galactonolactone, talonolactone), and
2,3,4,5,6,7-hexahydroxyheptanoic acid lactones (stereoisomers: alloheptonolactone, altroheptonolactone, glucoheptonolactone, mannoheptonolactone, guloheptonolactone, idoheptonolactone, galactoheptonolactone, taloheptonolactone).

(b) Aldaric Acid Lactones

Aldaric acids are polyhydroxy dicarboxylic acids derived from an aldose by oxidation of both terminal carbon atoms to carboxyl groups, and the acid of which can be represented by the following general formula:

$$HOOC(CHOH)_nCH(OH)COOH$$

where n is an integer from 1 to 4.

The aldaric acids form intramolecular lactones by removing one mole of water between one carboxyl group and one hydroxyl group.

The following are representative aldaric acid lactones:
2,3-dihydroxybutane-1,4-dioic acid lactones
2,3,4-trihydroxypentane-1,5-dioic acid lactoness (stereoisomers: ribarolactone, arabarolactone, xylarolactone, lyxarolactone);
2,3,4,5-tetrahydroxyhexane-1,6-dioic acid lactones (allarolactone, altrarolactone, glucarolactone, mannarolactone, gularic acid and gularolactone, idarolactone, galactarolactone, talarolactone);
2,3,4,5,6-pentahydroxyheptane-1,7-dioic acid lactones (stereoisomers: alloheptarolactone, altroheptarolactone, glucoheptarolactone, mannoheptarolactone, guloheptarolactone, idoheptarolactone, galactoheptarolactone, taloheptarolactone).

(c) Alduronic Acids

Alduronic acids are polyhydroxy acids resulting from oxidation of the alcohol group of an aldose to a carboxylic acid group, and can be represented by the following general formula:

$$HOOC(CHOH)_nCH(OH)CHO$$

where n is an integer from 1 to 4.

Many alduronic acids form intramolecular lactones by removing one mole of water between the carboxyl group and one hydroxyl group.

The following are representative alduronic acid lactones: riburonolactone; araburonolactone; xyluronolactone; lyxuronolactone; alluronolactone; altruronolactone; glucuronolactone; mannuronolactone; guluronolactone; iduronolactone; galacturonolactone; taluronolactone; allohepturonolactone; altrohepturonolactone; glucohepturonolactone; mannohepturonolactone; gulohepturonolactone; idohepturonolactone; galactohepturonolactone and talohepturonolactone.

(d) Aldobionic Acids

Aldobionic acids are also known as bionic acids, and typically include one monosaccharide chemically linked through an ether bond to an aldonic acid. Aldobionic acids may also be described as an oxidised form of a disaccharide or dimeric carbohydrate, such as lactobionic acid from lactose.

In most aldobionic acids, the carbon at position one of the monosaccharide is chemically linked to a hydroxyl group at a different position of the aldonic acid. Therefore, different aldobionic acids or stereoisomers can be formed from two identical monosaccharides and aldonic acids respectively.

As with acids (a) to (c) above, aldobionic acids have multiple hydroxyl groups attached to carbon chains.

Aldobionic acids can be represented by the following general formula:

$$H(CHOH)_m(CHOR)(CHOH)_nCOOH$$

where m and n are integers independently from 0 to 7 and R is a monosaccharide.

Aldobionic acids can form intramolecular lactones by removing one mole of water between the carboxyl group and one hydroxyl group.

The following are representative aldobionic acid lactones: lactobionolactone; and isolactobionolactone; maltobionolactone; isomaltobionic acid isomaltobionolactone; cellobionolactone; gentiobionolactone; kojibionolactone; laminaribionolactone; melibionolactone; nigerobionolactone; rutinobionolactone, and sophorobionolactone.

Preferably, the lactone is a delta lactone. More preferably the lactone is selected from gluconolactone, galactonolactone, glucuronolactone, galacturonolactone, gulonolactone, ribonolactone, saccharic acid lactone, pantoyllactone, glucoheptonolactone, mannonolactone, and galactoheptonolactone. Most preferably, the lactone is gluconolactone.

Mixtures of any of the above-described carbohydrate-derived acids may also be used in the composition of the invention.

The total amount of lactone in hair treatment compositions of the invention generally ranges from 0.01 to 20%, preferably from 0.01% to 2%, more preferably from 0.05 to 0.8% by total weight lactone based on the total weight of the composition.

Disaccharides

Suitable disaccharides preferably comprise of pentose or hexose sugars, more preferably the disaccharide comprises of two hexose units.

Disaccharides can be either reducing or non-reducing sugars. Non-reducing sugars are preferred.

The D(+) form of the disaccharides are preferred. Particularly preferred are trehalose and cellobiose or mixtures thereof. Trehalose is the most preferred disaccharide.

The level of disaccharides present in the total formulation from 0.001 to 8 wt % of the total composition, preferably from 0.005 wt % to 5 wt %, more preferably from 0.01 to 3 wt %, most preferably from 0.05 wt % to 2 wt %.

Inorganic Salt

Preferably, the composition according to the invention comprises inorganic salt.

In one preferred embodiment the inorganic salt is an alkali metal salt, preferably the alkali metal salt is a sulphate, most preferably it is sodium sulphate.

The inorganic salt is present at a level from 0.001 wt % of the total composition, preferably from 0.05 wt %, most preferably from 0.01 wt %. The maximum level of salt is less than 10 wt %, preferably less than 7 wt %, more preferably less than 5 wt %.

In a second alternatively preferred embodiment the inorganic salt is a source of ammonium ions, preferably this is ammonium carbonate.

This second preferred inorganic salt is preferably present at a level from 0.01 wt % of the total composition, more preferably from 0.05 wt %. The maximum level of ammonium carbonate is preferably less than 10 wt %, more preferably less than 5 wt %, most preferably less than 1 wt %. It is further preferred if the level of ammonium carbonate is from 0.01 to 2.0 wt % of the total composition.

Diacids

Di-acids may be present in the compositions of the present invention. Particularly suitable are di-acids having the formula:

$$HOOC-(CH_2)_n-COOH$$

where n is an integer from 2 to 8, more preferably where n equal to 2 or 4 (succinic acid and adipic acid respectively).

Di-acids are best used at levels in the total formulation from 0.01 wt % to 5 wt % of the total composition, more preferably at levels from 0.01 wt % to 2 wt %.

Where present, the weight ratio of di-acid to disaccharide is 1:10 to 20:1, more preferably 1:5 to 5:1.

In addition, acids are best used at di-acid:disaccharide molar ratios of between 0.1:1 and 10:1, preferably between 0.1:1 and 2:1.

The pH Adjuster

The pH of the compositions of the invention is from 2 to 4.5, preferably from 3 to 4.5.

We have found that the pH manipulates flow characteristics (thickness) of the gel. It is also important for the delivery of the fibre actives.

The pH of the composition comprises a pH adjuster. Suitable examples include sodium hydroxide, calcium hydroxide, citric acid, lactic acid and glycolic acid.

The Dye

The dye comprises violet, blue, red or mixtures thereof. This dye neutralizes the yellowing associated with the inclusion of protein materials.

Other Ingredients

The compositions of the invention may comprise a hair or skin benefit agent.

The hair or skin benefit agents may be single compounds or materials or mixtures of different compounds or materials. The mixture or each benefit agent is capable of imparting beneficial properties when used in a hair or skin treatment produc. Benefits include, for example, hair conditioning, hair colouring, hair styling and antidandruff benefits. Hair conditioning benefits are particularly preferred. For skin, preferred benefits are skin lightening, moisturisation and softening.

The benefit agent can be hydrophilic or hydrophobic.

The one or more hair benefit agents are present in a sufficient amount to perform the intended function, typically in an amount of about 0.1% to about 30% by weight of the composition.

Examples of suitable benefit agents include, but are not limited to, hair and skin conditioners, hair and skin cleansers, hair fixatives (including hair styling polymers), hair dyes, hair growth promoters, deodorants, skin care compounds, permanent wave compounds, hair relaxers, hair straighteners, antibacterial compounds, antifungal compounds, anti-inflammatory compounds, topical anesthetics, sunscreens and other cosmetic and medicinal topically-effective compounds. Preferably, skin compositions comprise silicone elastomer.

Hydrophobic oils, such as hydrocarbon oils, esters containing from 8 to 30 carbon atoms and particularly silicone oils, are preferred hair benefit agents. Other suitable oils are conditioning oils, preferably coconut oil.

Preferred optional ingredients include a conditioning oil, a preservative, a fragrance, a humectant and mixtures thereof.

A preferred humectant is propylene glycol.

The Composition

The composition of the invention is a cosmetic or personal care composition, for use on hair and/or skin. Examples include personal wash compositions such as soaps and shower gels. Preferably, the composition is a hair treatment composition such as a serum, tonic, gel, leave-in conditioner or mousse, leave in treatment, masque, rinse off treatment or lotion.

Hair Compositions

Hair treatment compositions of the invention include, for example, shampoos, conditioners, hair styling products, tonics and lotions.

Shampoo compositions of the invention comprise from 1% to 50%, preferably from 1% to 30%, more preferably from 5% to 30%, by weight of one or more surfactants.

Conditioners, also termed hair conditioning compositions, comprise from 0.1% to 30% preferably from 1% to 20%, more preferably from 2% to 15%, by weight of one or more hair conditioning agents.

Hair styling compositions comprise from 0.1% to 10%, preferably from 1% to 10%, more preferably from 2% to 8% by weight of one or more hair styling polymers.

Compositions of the invention can be leave on or rinse off compositions, preferably leave in. Rinse off compositions are intended to be rinsed from the hair after use, although a minor proportion of the composition, including at least some of the particles, will remain on the hair after rinsing. Leave on products are applied to the hair and need not be rinsed off the hair after this application.

Process for Preparation

The compositions of the invention can be prepared by the following process comprising the following steps:—

The polymeric thickener is added to water and mixed until fully dispersed.

Proteins and other water soluble components, such as the active materials (e.g. disaccharides or lactones) are then added to the mixture.

In a side vessel, oil based materials such as fragrance are blended with the solubiliser until mixed. This mixture is then added to the main batch and mixed until a transparent solution results.

In a side vessel, the dye component(s) are added to water and mixed until fully dissolved. The resulting dye mixture is added to the main vessel until fully mixed.

Finally, pH adjusters are added to the mixture until such time as the correct pH is achieved.

Skin and Hair Treatment Compositions

Examples of rinse off compositions of the invention are shampoo compositions and hair conditioning compositions.

Shampoo compositions of the invention comprise, in addition to the particles, at least one surfactant which provides a deterging benefit. The deterging surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts.

The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$-$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Examples include coco mono- or di-ethanolamide and coco mono-isopropanolamide.

Further nonionic surfactants which can be included in shampoos for the invention are the alkyl polyglycosides (APGs). Typically, the APG is one, which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group. Suitable alkyl polyglycosides for use in the invention are commercially available and include for example those materials identified as: Oramix NS10 ex Seppic; Plantaren 1200 and Plantaren 2000 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 1 to 50% by weight of the composition, preferably from 1 to 30% by weight, more preferably from 5 to 30% by weight.

Compositions in accordance with the invention may also take the form of hair conditioning compositions, which may be rinse off or leave-on hair conditioning compositions or so-called 2 in 1 compositions containing shampoo and conditioner. The conditioning compositions preferably comprise, in addition to the particles, one or more cationic surfactants. The use of cationic surfactants is especially preferred, because these ingredients are capable of providing conditioning benefits to hair.

Examples of cationic surfactants include the quaternary ammonium compounds mentioned hereinbefore as optional components of the hydrophilic phase. These include: quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethyl ammonium hydroxide, hexadecyltrimethylammonium hydroxide, cetyltrimethylammonium hydroxide, octyldimethylbenzylammonium hydroxide, decyldimethyl-benzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof containing anions other than hydroxide, e.g., chlorides, Cetylpyridinium hydroxide or salts thereof (e.g., chloride), Quaternium-5, Quaternium-31, Quaternium-18, and mixtures thereof.

In hair conditioning compositions according to the invention, the level of cationic surfactant is preferably from 0.01 to 10%, more preferably 0.05 to 5%, most preferably 0.1 to 2% by weight of the composition.

Hair conditioning and shampoo compositions of the invention may both also contain one or more additional conditioning agents, preferably selected from silicones, protein hydrolysates and quaternised protein hydrolysates and other materials which are known in the art as having desirable hair conditioning properties.

Silicones are the most preferred conditioning agents. The silicones are preferably in the form of liquid droplets, typically dispersed in compositions of the invention, preferably in an amount of from 0.01% to 5% by weight of the composition, more preferably from 0.1% to 5% by weight Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution. Alternatively, the high viscosity material may be in the form of an emulsion in water. The emulsion may be of high viscosity oil or of a solution of gum in a lower viscosity oil. The particle size of the oil phase may be anywhere in the range from 30 nanometers to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition. Advantageously, a silicone with a viscosity in the range 1-20 million cst is used. The silicone can be cross-linked.

Preferred silicones include polydimethylsiloxanes (of CTFA designation dimethicone) and hydroxylated polydimethylsiloxanes (of CTFA designation dimethiconol). Silicones of the above types are widely available commercially, for example as DC-1784 and DCX2-1391, both ex Dow Corning.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

In accordance with the invention, the hair shampoo and/or conditioner composition may also comprise a polymeric water-soluble cationic polymer as a conditioning agent.

The cationic polymer may be present at levels of from 0.01 to 5%, preferably from about 0.05 to 1%, more preferably from about 0.08% to about 0.5% by weight.

Synthetic or naturally derived polymers having a quaternised nitrogen atom are useful. The molecular weight of the polymer (in g/mol) will generally be between 5 000 and 10 000 000, typically at least 10 000 and preferably in the range 100 000 to about 2 000 000.

Representative synthetic quaternised polymers include, for example: cationic copolymers of 1-vinyl-2-pyrrolidine and 1-vinyl-3-methyl-imidazolium salt (e.g., chloride salt) (referred to in the industry by the Cosmetic, Toiletry, and Fragrance Association, "CTFA", as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyldiallylammonium chloride homopolymer (referred to in the industry (CTFA) as Polyquaternium 6); mineral acid salts of amino-alkyl esters of homo- and co-polymers of unsaturated carboxylic acids having from 3 to 5 carbon atoms, as described in U.S. Pat. No. 4,009,256; and cationic polyacrylamides as described in WO95/22311.

Representative naturally-derived quaternised polymers include quaternised cellulosic compounds and cationic guar gum derivatives, such as guar hydroxypropyltrimonium chloride. Examples are JAGUAR C-13S, JAGUAR C-15, and JAGUAR-C17, commercially available from Meyhall in their JAGUAR (trademark) series.

Suitable cationic polyacrylamides are described in WO 95/22311 whose contents are incorporated herein by reference.

The compositions may further comprise from 0.1 to 5% of a suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. A further suitable suspending agent is dihydrogenated tallow phthalic acid amide (available from Stepan under the trademark Stepan TAB-2).

Suitable cross linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into shampoo and/or conditioning compositions of the invention is a fatty alcohol material. The use of these materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

A further ingredient that may be desirably included in the shampoo and/or conditioning compositions is a pearlescent material. Suitable pearlescent materials include ethylene glycol distearate, ethylene glycol monostearate, guanine and titanium dioxide coated micas, bismuth oxychloride, and stearic monoethanol amide. The level of pearlescent material present in the composition is generally 0.1% to 5%, preferably from 0.3% to 3% by weight of the composition.

Antimicrobial Agents

The compositions of the invention may optionally comprise an antimicrobial agent. The antimicrobial agent may be a single compound or a mixture of two or more compounds.

The antimicrobial agent may, for example, be in solid particulate form or dissolved in compositions of the invention.

The antimicrobial agent is typically present in compositions of the invention in an amount of from 0.01% to 5% by weight, preferably from 0.1% to 2% by weight.

Preferably, soluble antimicrobial agents are selected from climbazole, ketoconazole, octapirox and mixtures thereof. More preferably, the antimicrobial agent is climbazole. These antimicrobial agents will typically be in solution in compositions of the invention.

The preferred solid antimicrobial agents are metal pyrithiones, particularly zinc pyrithione (ZnPTO) which, on account of its relative insolubility in aqueous systems, is generally used in hair treatment compositions as a particulate dispersion. The zinc pyrithione may be used in any particle form including, for example, crystalline forms such as platelets and needles and amorphous, regularly or irregularly shaped particles. If zinc pyrithione is present in the composition, a suspending agent is preferably used to prevent or inhibit the settling of the particles out of the composition. The average particle diameter of the zinc pyrithione particles (ie, their maximum dimension) is typically from about 0.2 to about 50 μm, preferably from about 0.4 to about 10 μm. Particle size can be measured using a Malvern Mastersizer (Malvern Instruments, Malvern, UK).

Antimicrobial agents typically display a minimum inhibitory concentration of about 50 mg/ml or less against *Malassezia*.

The shampoo and/or conditioner compositions of the invention are preferably aqueous based. The compositions suitably comprise water in amount of from about 20 to about 99% by weight of the total composition.

The shampoo and conditioner compositions of the present invention may also contain other ingredients conventionally used in the art such as diluents, sequestrants, thickeners, carriers, antioxidants, proteins, polypeptides, preservatives, moisturizing agents, solvents, perfumes, enzymes and polymers.

emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.

vitamins and derivatives thereof (e.g., ascorbic acid, vitamin E, tocopheryl acetate, retinoic acid, retinol, retinoids, and the like).

cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).

preservatives, antioxidants, chelators and sequestrants; and aesthetic components such as fragrances, colorings, hair nutrients and essential oils.

Perfumes

It is preferred that the compositions of the invention comprise a perfume (also called herein fragrance), which includes pro-fragrances.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damascenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil. Perfume components which are odiferous materials are described in further detail below.

The perfume is typically present in an amount of from 0.01 to 5% by total weight of the composition, preferably from 0.1 to 2% by total weight of the composition. The perfume suitably has a molecular weight of from 50 to 500 Dalton. Pro-fragrances can be of higher molecular weight, being typically 1-10 kD.

Useful components of the perfume include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the particle.

Typical perfume components which it is advantageous to employ in the embodiments of the present invention include those with a relatively low boiling point, preferably those with a boiling point of less than 300, preferably 100-250 Celsius.

It is also advantageous to include perfume components which have a low Log P (i.e. those which will be partitioned into water), preferably with a Log P of less than 3.0. These materials, of relatively low boiling point and relatively low Log P have been called the "delayed blooming" perfume ingredients and include the following materials: Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine. It is commonplace for a plurality of perfume components to be present in a formulation, for example, four or more, preferably five or more, more preferably six or more or even seven or more different perfume components.

Subject to the aforementioned constraints, the respective fragrances can comprise any perfume component or preferably a mixture of components. Each fragrance commonly comprises at least 6 components, particularly at least 12 components and often at least 20 components.

The perfume component oils herein commonly have a ClogP value of at least 0.1 and often at least 0.5.

Representative fragrance oils having a boiling point of below 250° C. at 1 bar pressure include the following materials:—anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, iso propyl quinoline, 2,6-nonadien-1-al, 2-methoxy-3-(2-methylpropyl)-pyrazine, methyl octine carbonate, thdecene-2-nithle, allyl amyl glycolate, cyclogalbanate, cyclal C, melonal, gamma nonalactone, cis 1,3-oxathiane-2-methyl-4-propyl, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinaool, verdox, and cis-3-hexenyl acetate.

Representative fragrance oils having a boiling point at 1 bar pressure of at least 250° C. include:—ethyl methyl phenyl glycidate, ethyl vanillin, heliotropin, indol, methyl anthranilate, vanillin, amyl salicylate, coumarin, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral, intreleven aldehyde eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate. The fragrances employed herein, can comprise a pre-formed blend, either extracted from natural products, or possibly created synthetically. Representatives of such pre-formed blends include oils from:—Bergamot, cedar atlas, cedar wood, clove, geranium, guaiac wood, jasmine, lavender, lemongrass, lily of the valley, lime, neroli, musk, orange blossom, patchouli, peach blossom, petitgrain or petotgrain, pimento, rose, rosemary, and thyme.

EXAMPLES

The invention will now be illustrated by the following non-limiting examples. In the examples and throughout this specification, all percentages are by weight based on total composition unless indicated otherwise.

Example 1: Composition T1, in Accordance with the Invention, and Comparative Composition TA Compositions T1 and TA were manufactured using the following method:—
The polymeric thickener was added to water and mixed until fully dispersed.
The hydrolysed proteins, trehalose, sodium sulphate, adipic acid, gluconolactone and other water soluble materials were then added to the mixture.
In a separate vessel, the fragrance and other oil soluble materials were blended with the solubiliser.

This mixture was then added to the main batch and mixed until a transparent solution was obtained.
In a side vessel, the dye component(s) were added to water and mixed until fully dissolved. The resulting dye mixture was added to the main vessel and fully mixed.
Finally, the pH was adjusted with sodium hydroxide to between 3 and 4.5.
The compositions are shown in Table 1.

TABLE 1

Compositions of T1 and TA (wt %)

| Ingredient | Composition T1 (in accordance with the invention) (wt %) | Comparative composition TA (wt %) |
|---|---|---|
| Hydrolysed elastin[1] | 0.1 | 0.1 |
| Hydrolysed keratin[2] | 0.4 | 0.4 |
| Sodium hydroxide (50%) | 0.4 | 0.4 |
| Glycerine[3] | 3.0 | 3.0 |
| Perfume | 0.25 | 0.25 |
| Eumulgin HPS emulsifier[2] | 1.5 | — |
| Trehalose | 0.23 | 0.23 |
| Sodium sulphate | 0.1 | 0.1 |
| D-Gluconolactone | 0.01 | 0.01 |
| Adipic acid | 0.01 | 0.01 |
| PVM/MA decadiene crosspolymer[4] | 0.7 | 0.7 |
| Red33 (dye) | 0.08 | — |
| Blue (dye) | 0.07 | — |
| Deionised water | To 100 | To 100 |

[1]Ex Lonza
[2]Ex BASF
[3]Pricerine 9091, available from Croda
[4]Stabileze QM, ex Ashland Inc

Example 2: Colour Stability of Compositions T1 and TA

Compositions T1 and TA were stored at a range of temperatures (5° C., 25° C., 37° C. and 45° C.) for a period of 4 weeks. During this time it was noticed that T1 remained clear and free of yellow discoloration when compared to TA which became increasingly turbid and yellowed over time.

The invention claimed is:
1. A transparent cosmetic or personal care composition comprising:
   a) a polymeric thickener comprising a copolymer of vinyl methyl ether and maleic anhydride,
   b) a protein,
   c) an active material, which is selected from disaccharides, lactones, inorganic salts, diacids and mixtures thereof,
   d) a solubiliser,
   e) a pH adjuster,
   f) a dye
   g) water, and
   h) fragrance
   the composition being a leave-on hair treatment composition in the form of a gel, wherein the solubiliser comprises a mixture of at least two components, said mixture comprising at least one high HLB component having an HLB value of from 10 to 20 and at least one low HLB component having an HLB value of from 1 to less than 10, the mixture comprising Coceth-7, PPG-1 PEG-9 Lauryl Glycol Ether and PEG-40 Hydrogenated Castor Oil,
   and wherein the dye comprises violet, blue, red or mixtures thereof, and wherein the composition has a pH in the range of from 2 to 4.5.

2. A transparent composition as claimed in claim 1, wherein the copolymer of vinyl methyl ether and maleic anhydride is polyvinylmethylether/maleicanhydride decadiene crosspolymer.

3. A transparent composition as claimed in claim 1, wherein the protein is selected from hydrolysed keratin, hydrolysed wheat protein, hydrolysed roe, caviar, hydrolysed elastin, hydrolysed collagen and mixtures thereof.

4. A transparent composition as claimed in claim 1, wherein the disaccharide is trehalose.

5. A transparent composition as claimed in claim 1, wherein the lactone is gluconolactone.

6. A transparent composition as claimed in claim 1, wherein the inorganic salt is sodium sulphate.

7. A transparent composition as claimed in claim 1 which comprises an additional ingredient selected from an oil, a preservative, a humectants and mixtures thereof.

8. A method of treating hair, comprising applying to the hair a transparent composition as defined by claim 1.

* * * * *